(12) United States Patent
Kang et al.

(10) Patent No.: US 9,018,349 B2
(45) Date of Patent: Apr. 28, 2015

(54) PROCESS FOR PREPARING CASPOFUNGIN AND NOVEL INTERMEDIATES THEREOF

(75) Inventors: Heui-Il Kang, Gunpo-si (KR); Yun-Beom Ham, Ansan-si (KR); Su-Hyun Kyong, Anyang-si (KR); Heung-Mo Kang, Seoul (KR); Tae-Hee Han, Hwaseong-Si (KR); Doo-Jin Kang, Ansan-si (KR)

(73) Assignee: CKD Bio Corp., Seoul (KR)

( * ) Notice: Subject to any disclaimer, the term of this patent is extended or adjusted under 35 U.S.C. 154(b) by 0 days.

(21) Appl. No.: 13/881,204

(22) PCT Filed: Jan. 12, 2011

(86) PCT No.: PCT/KR2011/000196
§ 371 (c)(1),
(2), (4) Date: Jun. 12, 2013

(87) PCT Pub. No.: WO2012/077853
PCT Pub. Date: Jun. 14, 2012

(65) Prior Publication Data
US 2013/0261286 A1  Oct. 3, 2013

(30) Foreign Application Priority Data
Dec. 9, 2010  (KR) .................. 10-2010-0125641

(51) Int. Cl.
| | |
|---|---|
| A61K 38/12 | (2006.01) |
| C07K 5/00 | (2006.01) |
| C07K 7/00 | (2006.01) |
| C07K 16/00 | (2006.01) |
| C07K 17/00 | (2006.01) |
| C07K 7/56 | (2006.01) |
| C07D 487/14 | (2006.01) |

(52) U.S. Cl.
CPC ............ C07K 7/56 (2013.01); C07D 487/14 (2013.01)

(58) Field of Classification Search
CPC .................................. A61K 38/00; C07K 7/56
See application file for complete search history.

(56) References Cited

U.S. PATENT DOCUMENTS

| | | |
|---|---|---|
| 5,194,377 A | 3/1993 | Schwartz et al. |
| 5,202,309 A | 4/1993 | Schwartz et al. |
| 5,378,804 A | 1/1995 | Balkovec et al. |
| 5,514,650 A | 5/1996 | Balkovec et al. |
| 5,552,521 A | 9/1996 | Belyk et al. |
| 5,854,213 A | 12/1998 | Bouffard |
| 5,936,062 A | 8/1999 | Leonard et al. |
| 2004/0158034 A1 | 8/2004 | Belyk et al. |
| 2008/0319162 A1 | 12/2008 | Ludescher et al. |
| 2009/0291996 A1 | 11/2009 | Korodi et al. |

FOREIGN PATENT DOCUMENTS

WO   WO 2009151341 A1 * 12/2009

OTHER PUBLICATIONS

Ethylenediamine, Wayback machine captured on Jun. 16, 2008.*
Leonard, Jr., William R. et al., Synthesis of the Antifungal β-1,3-Glucan Synthase Inhibitor Cancidas (Caspofungin Acetate) from Pneumocandin B0β, J. Org. Chem,. 2007, vol. 72, pp. 2335-2343.
International Search Report for PCT/KR2011/000196 dated Feb. 6, 2012.

* cited by examiner

*Primary Examiner* — Marcela M Cordero Garcia
*Assistant Examiner* — Kaipeen Yang
(74) *Attorney, Agent, or Firm* — Heslin Rothenberg Farley & Mesiti P.C.; Andrew K. Gonsalves, Esq.

(57) ABSTRACT

The present invention relates to a novel process for preparing the aza cyclohexapeptide compound 1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$ (caspofungin) represented by the following formula 1, which can improve the problem due to a pungent odor and toxicity during the process and can prepare caspofungin as a final product at high yield compared to conventional processes, and to novel intermediates which are used in the preparation process:

[Formula 1]

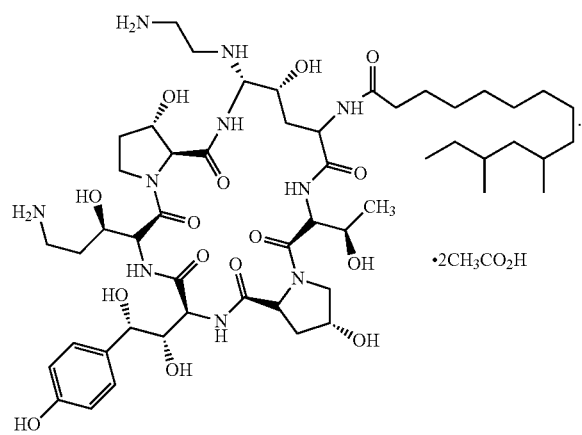

7 Claims, No Drawings

PROCESS FOR PREPARING CASPOFUNGIN AND NOVEL INTERMEDIATES THEREOF

CROSS REFERENCE TO RELATED APPLICATION

This application is the National Phase filing of International Application No. PCT/KR2011/000196, filed Jan. 12, 2011, which claims priority to Korean Application No. 10-2010-0125641, filed Dec. 9, 2010. The entire content of each prior application is hereby incorporated by reference.

TECHNICAL FIELD

The present invention relates to a novel process for preparing caspofungin (aza cyclohexapeptide compound), which can improve the problem due to a pungent odor and toxicity during the process and can prepare caspofungin as a final product at high yield compared to conventional processes, and to novel intermediates which are used in the preparation process.

BACKGROUND ART

Caspofungin is represented by formula 1 below and has the chemical name 1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$. Caspofungin is a macrocyclic lipopeptide belonging to the echinocandin family, a new class of antifungal agents that inhibits the biosynthesis of beta (1,3)-D-glucan, an integral component of the fungal cell wall. It is useful in treating systemic fungal infections, especially those caused by *Candida, Aspergillus, Histoplasma, Coccidioides* and *Blastomyces*. It has also been found to be useful for the treatment and prevention of infections caused by *Pneumocystis carinii* which are often found in immunocompromised patients such as those with AIDS.

[Formula 1]

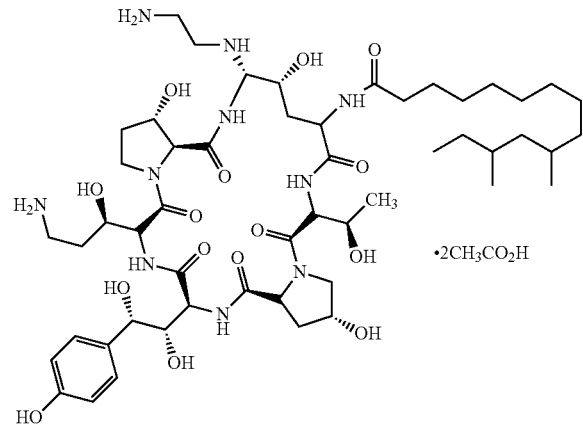

The compound 1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$ and its pharmaceutically acceptable salts are known under the INN caspofungin (see Merck Index, 13th edition, monograph no. 1899).

Processes for preparing caspofungin are described in U.S. Pat. No. 5,378,804, U.S. Pat. No. 5,514,650, U.S. Pat. No. 5,552,521, US 2009/0291996, US 2008/0319162, and U.S. Pat. No. 5,936,062.

U.S. Pat. No. 5,378,804, issued to Merck & Co., Inc. (Rahway, N.J.), discloses aza cyclohexapeptide compounds as caspofungin and fundamental steps of synthesizing caspofungin.

U.S. Pat. No. 5,514,650 discloses: a process comprising allowing alkylthiol or arylthiol to react with, for example, aminoethylthiol from pneumocandin $B_0$, and oxidizing the reaction product to a sulfone intermediate which is then allowed to react with an amine compound, for example, a diamine compound such as ethylenediamine, in an anhydrous aprotic solvent; and a process of isolating the reaction product by chromatography. However, the disclosed process is uneconomical, because the time of reaction of alkylthiol or arylthiol with pneumocandin $B_0$ is long and several chromatographic processes are required to purify the intermediate and the final product, thus reducing the overall synthesis yield.

U.S. Pat. No. 5,552,521 discloses a process of obtaining aza cyclohexapeptide compounds, for example, caspofungin, by reducing the primary amide functional group of pneumocandin $B_0$ to the corresponding amine group and then allowing the reduced compound to react with thiophenol and then with ethylenediamine. However, the yield of the reduction step was reported to be about 43%, and the pungent odor and strong toxicity of thiophenol during the introduction thereof make it difficult to carry out the process. In addition, the step of reaction with thiophenol has a low yield of not more than 70%, and for this reason, the overall yield of the process is not more than 10%.

US 2009/0291996 discloses a preparation process comprising three synthesis reaction steps of synthesizing caspofungin from pneumocandin $B_0$ and two column chromatographic purification steps, wherein the synthesis reaction steps are carried out based on the literature (Leonard et al., *J. Org. Chem.* 2007, 72, 2335-2343) that describes the actual preparation process in detail. However, as described therein, the synthesis steps provide caspofungin having a purity of not less than 99.0% at a yield of 21.2%. Thus, when a process for increasing the purity of caspofungin is carried out, the yield of caspofungin will be significantly decreased.

US 2008/0319162 discloses a process of converting an amide functional group to a cyano group which is then reduced to the corresponding amine group through hydrogenation, wherein the process is carried out based on the literature (Journet et al., *J. Org. Chem.* 1999, 64, 2411-2417) which describes an improved process for reducing the primary amide functional group of pneumocandin $B_0$. However, this preparation process needs to be carried out under strictly anhydrous conditions, because the control of water content during a dehydrogenation reaction that is carried out by cyanuric chloride at −30° C. can greatly affect the reaction efficiency. Also, equipment for separating the compounds at low temperature under reduced pressure is required, and a multi-step chromatographic process is used to purify the intermediates and the final product. For this reason, the overall yield of the process was reported to be not more than 10%.

U.S. Pat. No. 5,936,062 discloses two stereoselective processes that use pneumocandin $B_0$ as a starting material. The first process comprises reducing the primary amide functional group of pneumocandin $B_0$ to the corresponding amine group using phenylboronate as a protecting group and allowing the reduced intermediate to react with phenylthiol and then with ethylenediamine. The second process comprises reducing the primary amide functional group of an intermediate, having an S-aryl moiety at the 5-orn position, to the corresponding amine in the presence of phenylboronate as a protecting group, and then allowing the reduced intermediate to react with, for example, ethylenediamine. The intermediate compound, obtained by crystallizing the reaction product in an acidic condition and then reducing the amide group to an amine group, was reported to have a reaction yield of about 61% (HPLC assay).

Accordingly, it is required to develop an improved process which can prepare caspofungin in an environmentally friendly and economical manner.

DISCLOSURE OF THE INVENTION

Technical Problem

As described above, the processes according to the prior art could not be easily applied at an industrial scale, because they were complex or risky. Particularly, thiol derivatives containing an aromatic ring have been used in the prior art processes, because a resonance structure needs to be formed through the aromatic ring such that the thiol substituent of the thiol intermediate is easily removed in the final removal step. However, such processes have a pungent odor, strong toxicity and a relatively low yield, and for this reason, there has been a need for a process that uses an improved thiol substituent. Accordingly, the present invention has been made in order to solve the above-described problems occurring in the prior art, and it is an object of the present invention to prepare pharmaceutically active aza cyclohexapeptide compounds for antifungal applications at high yield by preparing novel intermediates without risk factors or process troubles and improving the convenience and productivity of the preparation process.

Technical Solution

To achieve the above object, the present invention provides a preparation process represented by the following reaction scheme 1:

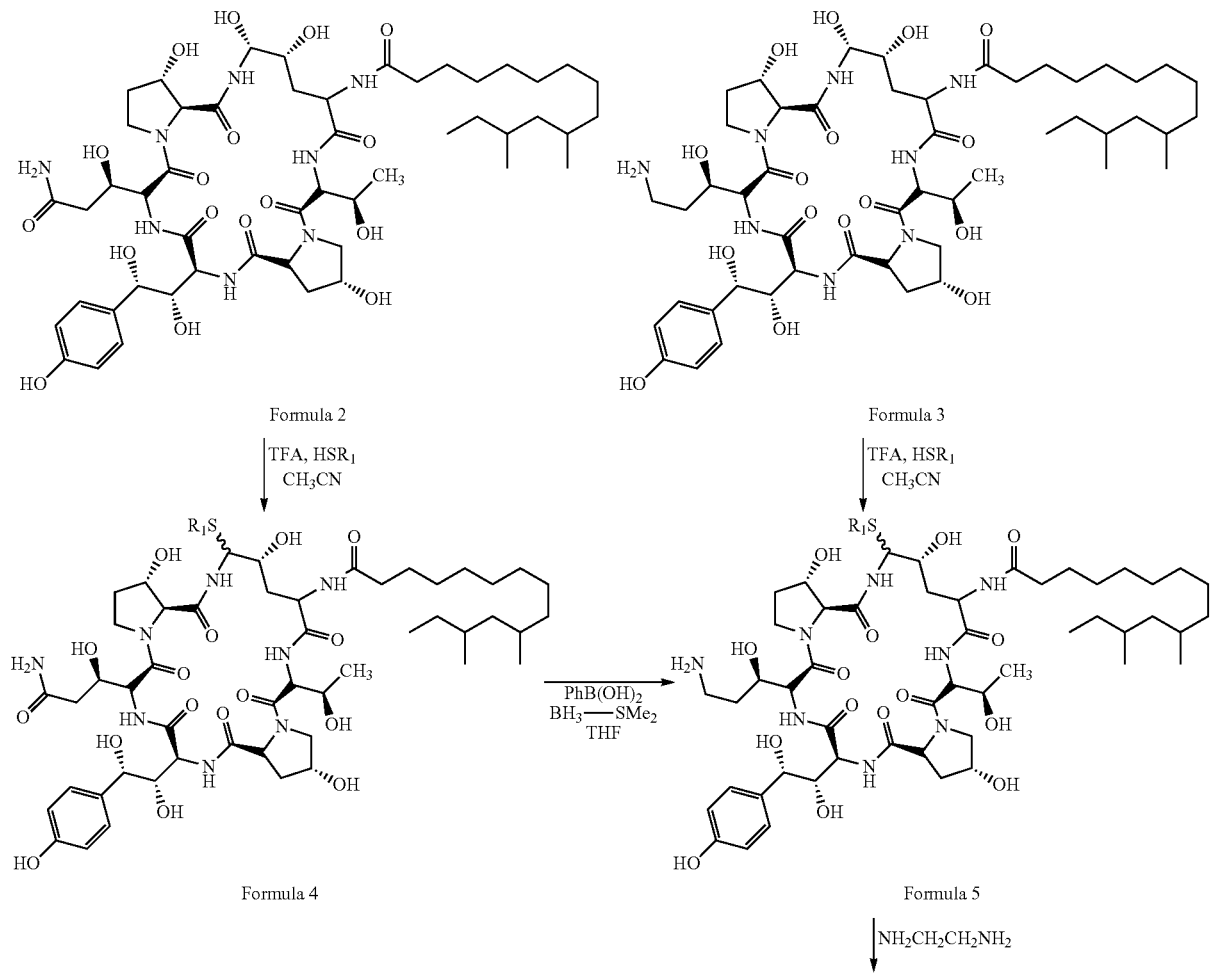

-continued

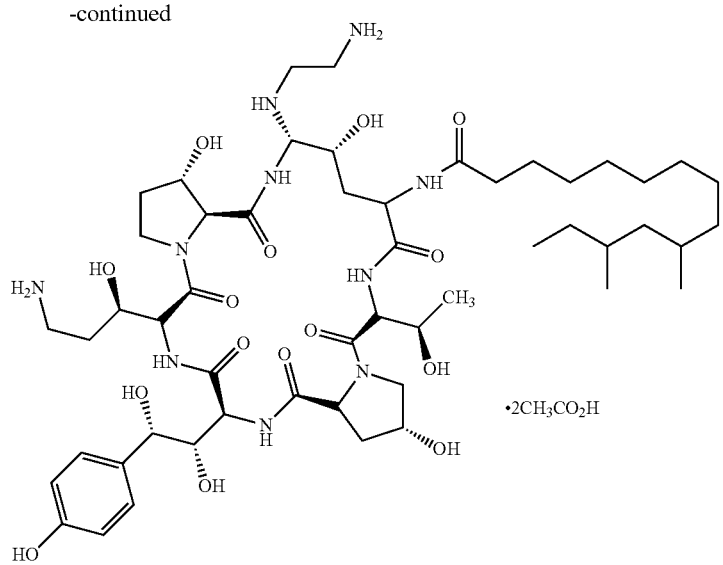

Formula 1 wherein $R_1$ is a tetrazole ring or a tetrazole derivative containing four nitrogen atoms, $-(CH_2)_n C(=O)OR_2$, or $-(CH_2)_m C(=O)NH(CH_2)_m NH_2$ (wherein $R_2$ is H or $C_1$-$C_3$ alkyl, n=1, 2 or 3; m=1, 2 or 3).

Accordingly, the present invention provides the followings:

(1) A process of preparing a compound of the following formula 1 or an acid addition salt thereof comprising the step of reacting a compound of the following formula 5 with 1,2-diaminoethane:

[Formula 1]

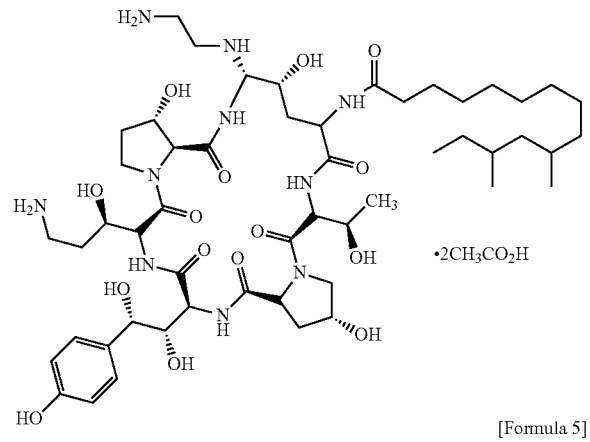

[Formula 5]

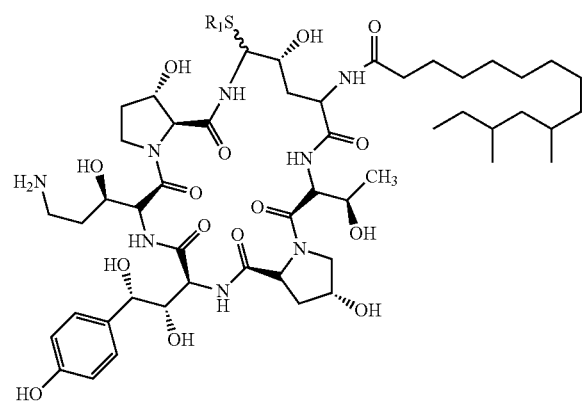

wherein $R_1$ is a tetrazole ring or a tetrazole derivative containing four nitrogen atoms, $-(CH_2)_n C(=O)OR_2$, or $-(CH_2)_m C(=O)NH(CH_2)_m NH_2$ (wherein $R_2$ is H or $C_1$-$C_3$ alkyl, n=1, 2 or 3; m=1, 2 or 3);

(2) The process according to (1), wherein $R_1$ is a tetrazole ring or a tetrazole derivative containing four nitrogen atoms;

(3) The process according to (1), wherein the process further comprises the steps of:

a) reacting a compound of the following formula 2 with a compound of $HSR_1$ to obtain a sulfide compound of the following formula 4; and b) reducing the compound of formula 4 as obtained in step a) to obtain the compound of formula 5:

[Formula 2]

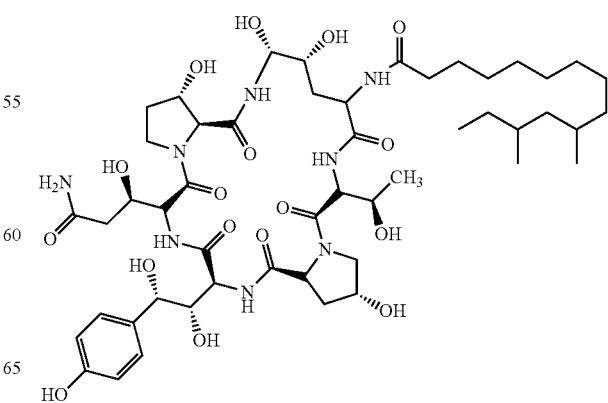

-continued

[Formula 4]

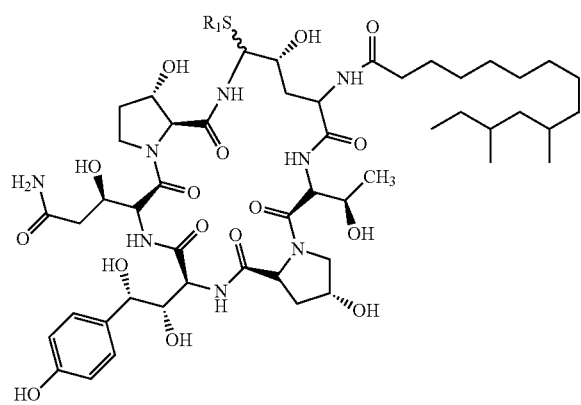

wherein $R_1$ is a tetrazole ring or a tetrazole derivative containing four nitrogen atoms, —$(CH_2)_1C(=O)OR_2$, or —$(CH_2)_mC(=O)NH(CH_2)_mNH_2$ (wherein $R_2$ is H or $C_1$-$C_3$ alkyl, n=1, 2 or 3; m=1, 2 or 3);

(4) The process according to (1), wherein the process further comprises a step of reacting a compound of the following formula 3 with a compound of $HSR_1$, wherein $R_1$ is a tetrazole ring or a tetrazole derivative containing four nitrogen atoms, —$(CH_2)_nC(=O)OR_2$, or —$(CH_2)_nC(=O)NH(CH_2)_mNH_2$ (wherein $R_2$ is H or $C_1$-$C_3$ alkyl, n=1, 2 or 3; m=1, 2 or 3), to obtain the compound of formula 5:

[Formula 3]

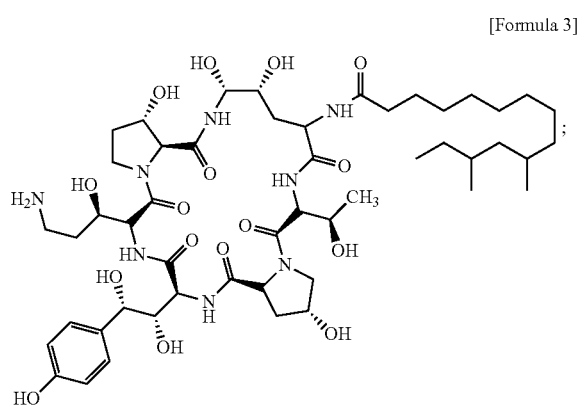

(5) The process according to (3), wherein the reducing in step b) is carried out using a borane complex or metal boride;

(6) The process according to (5), wherein the metal boride is $ZrCl_4/NaBH_4$ or $TiCl_4/NaBH_4$, and the borane complex is either a borane forming a complex with dimethylsulfide, dibenzylsulfide, diphenylsulfide, THF or 1,4-oxathiane, or $BH_2Cl$ forming a complex with dimethyl sulfide;

(7) The process according to (1), wherein the reaction with 1,2-diaminoethane is carried out using neat 1,2-diaminoethane or 1,2-diaminoethane dissolved in a solvent;

(8) The process according to (7), wherein the solvent is selected from among water, methanol, ethanol, tetrahydrofuran, isopropanol, trifluoroethanol, acetonitrile and dichloromethane;

(9) A compound of the following formula 4 or an acid addition salt or solvate thereof:

[Formula 4]

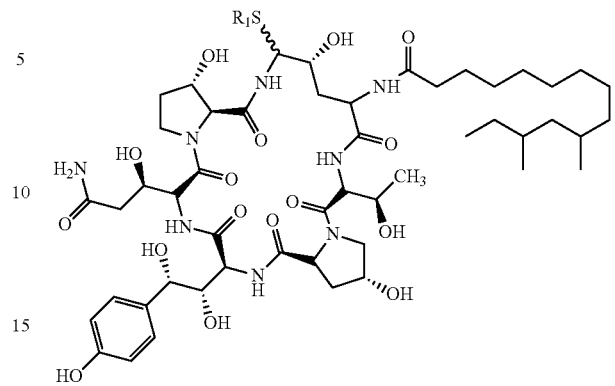

wherein $R_1$ is a tetrazole ring or a tetrazole derivative containing four nitrogen atoms, —$(CH_2)_1C(=O)OR_2$, or —$(CH_2)$—$C(=O)NH(CH_2)_mNH_2$ (wherein $R_2$ is H or $C_1$-$C_3$ alkyl, n=1, 2 or 3; m=1, 2 or 3);

(10) The compound according to (9), wherein $R_1$ is a tetrazole ring or a tetrazole derivative containing four nitrogen atoms;

(11) A compound of the following formula 5 or an acid addition salt or solvate thereof:

[Formula 5]

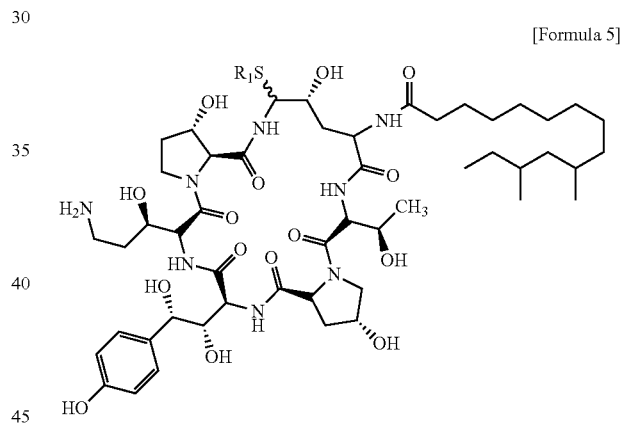

wherein $R_1$ is a tetrazole ring or a tetrazole derivative containing four nitrogen atoms, —$(CH_2)_1C(=O)OR_2$, or —$(CH_2)$—$C(=O)NH(CH_2)_mNH_2$ (wherein $R_2$ is H or $C_1$-$C_3$ alkyl, n=1, 2 or 3; m=1, 2 or 3);

(12) The compound according to (11), wherein $R_1$ is a tetrazole ring or a tetrazole derivative containing four nitrogen atoms.

Hereinafter, the specific construction and effect of the present invention will be described in detail with reference to the case in which $R_1$ in formula 4 and formula 5 is —$CH_2C(=O)OCH_3$.

The present invention relates to a process of preparing caspofungin (aza cyclohexapeptide compound) as a final product at high yield by increasing the production of novel thiol intermediates through a more efficient process wherein a thiol derivative, substituted with alkyl and tetrazole and having low pungent odor and toxicity, is introduced in place of thiol derivatives containing an aromatic ring, which could not be easily applied at an industrial scale due to a pungent odor and toxicity.

[Reaction scheme 2]
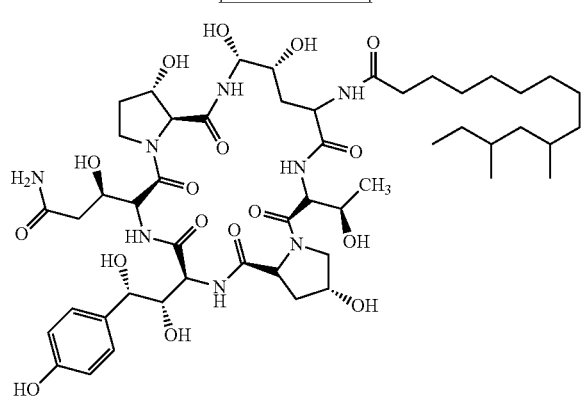
Formula 2
Methyl-2-mercaptoacetate
TFA, CH$_3$CN
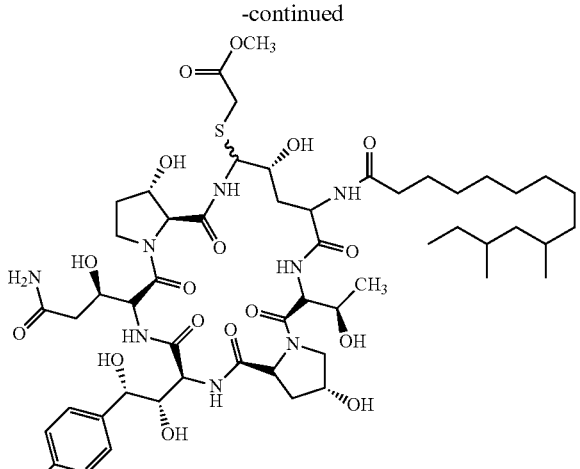
Formula 4
($R_1$ is CH$_2$C(=O)OCH$_3$)
[Reaction scheme 3]
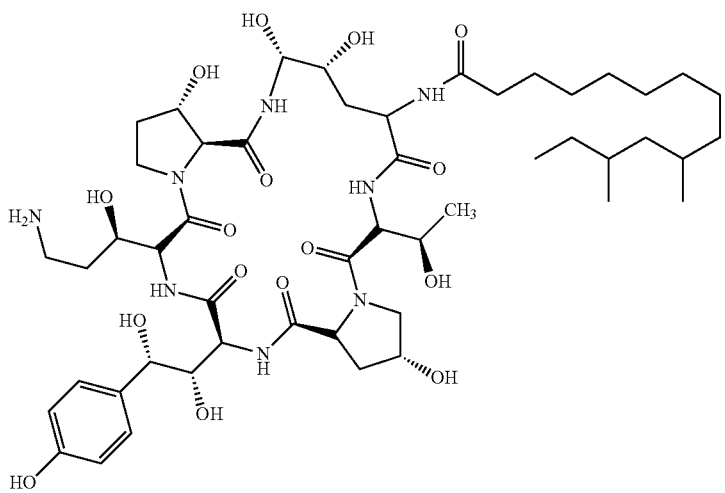
Formula 3
Methyl-2-mercaptoacetate
TFA, CH$_3$CN -continued

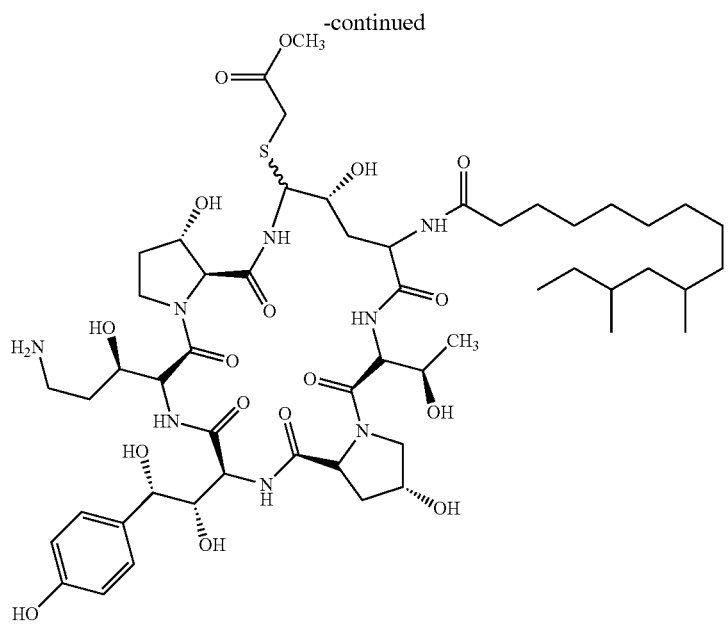

Formula 5
($R_1$ is $CH_2C(\!\!=\!\!O)OCH_3$)

Pneumocandin $B_0$ represented by formula 2 in the above reaction scheme 2 is a secondary metabolite produced by the fungus *Glarea lozoyensis* and serves as an intermediate in the production of caspofungin (see, for example, U.S. Pat. No. 5,194,377 and U.S. Pat. No. 5,202,309). Pneumocandin $B_0$ was named the compound 1-[4,5-dihydroxy-$N^2$-(10,12-dimethyl-1-oxotetradecyl)ornithine]-5-(3-hydroxyglutamine)-6-[3-hydroxy proline]echinocandin B, with its preferred stereoisomer being 1-[4,5-dihydroxy-$N^2$-(10,12-dimethyl-1-oxotetradecyl)-L-ornithine]-5-(3-hydroxy-L-glutamine)-6-[3-hydroxy-L-proline]echinocandin B, as described, e.g., in U.S. Pat. No. 5,202,309.

The compound of formula 3 in the above reaction scheme 3 is an intermediate which is obtained through conversion to a cyano group and hydrogenation from pneumocandin $B_0$ as disclosed in Journet et al., *J. Org. Chem.* 1999, 64, 2411-2417.

Specifically, as shown in the above reaction scheme 2 or reaction scheme 3, an organic solvent is added to a diol-containing intermediate having a structure of formula 2 or 3, and the solution is cooled. Then, organic acid and methyl-2-mercaptoacetate are added thereto, and the mixture is stirred at low temperature for about 6 hours. Then, purified water is added to the reaction solution, thus obtaining a precipitated product.

The amount of methyl-2-mercaptoacetate used in the reaction of reaction scheme 2 or reaction scheme 3 is 1.0-10.0 molar equivalents, and preferably 3.0-3.5 molar equivalents, relative to the moles of the diol-containing intermediate.

The organic acid used in the reaction of reaction scheme 2 or reaction scheme 3 is preferably trifluoroacetic acid and is used in an amount of 1.0-50.0 molar equivalents, and preferably 30.0-35.0 molar equivalents, relative to the moles of the diol-containing intermediate.

Solvents that may be used in the above reaction are nitrile solvents, such as acetonitrile and propionitrile. A preferred solvent is acetonitrile.

The solvent is used in a volume (ml) equal to 10.0-50.0 times the weight (g) of the diol-containing intermediate, and preferably in a volume (ml) equal to 20.0-25.0 times the weight (g) of the diol-containing intermediate.

The reaction of reaction scheme 2 or reaction scheme 3 may be carried out at a temperature ranging from –5° C. to 30° C., and preferably from 0° C. to 5° C.

The reaction of reaction scheme 2 or reaction scheme 3 is carried out for 1-24 hours, and preferably 6-8 hours. The amount of diol-containing intermediate remaining after completion of the reaction is not more than 10.0%, and preferably not more than 5.0%.

In the process of crystallizing the reaction product, when the compound of formula 2 was used, purified water is added in a volume (ml) equal to 1.0-90.0 times the weight (g) of the diol-containing intermediate, and preferably in a volume (ml) equal to 60.0-70.0 times the weight (g) of the intermediate, and when the compound of formula 3 was used, purified water is added in a volume (ml) equal to 0.5-5.0 times the weight (g) of the diol-containing intermediate, and preferably in a volume (ml) equal to 0.5-1.0 time the weight (g) of the intermediate.

The degree of progress of this reaction can be analyzed and determined by, for example, thin film chromatography or HPLC.

A process of obtaining the compound of formula 5 from the compound of formula 4 in which $R_1$ is —$CH_2C(\!\!=\!\!O)OCH_3$ is shown in the following reaction scheme 4.

[Reaction scheme 4]

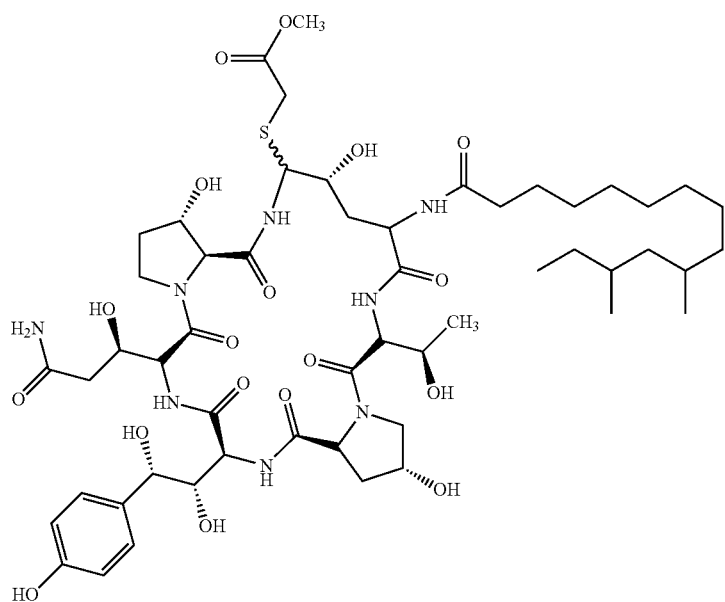

Formula 4
($R_1$ is $CH_2C(\!=\!O)OCH_3$)

1) $PhB(OH)_2$, $BH_3\text{-}SMe_2$, THF
2) aq HCl
3) RP HPLC

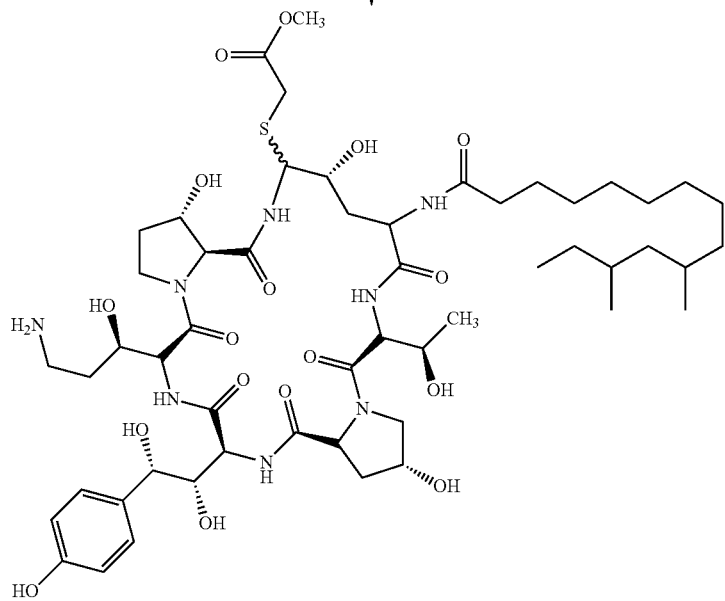

Formula 5
($R_1$ is $CH_2C(\!=\!O)OCH_3$)

As shown in the above reaction scheme 4, an organic solvent is added to the intermediate of formula 4, obtained in the previous step, and phenylboronic acid is added thereto. Then, water is removed from the mixture using a molecular sieve, and a borane dimethylsulfide complex is added as a reducing agent. Then, the mixture is stirred at low temperature for about 6 hours, and then neutralized with 2N hydrochloric acid solution at −15° C. Next, the resulting material is purified using a medium pressure column packed with a RP-C18 (Reverse Phase chromatography media—ODS silicagel) adsorbent, thus obtaining a product.

With respect to a borane complex or metal boride which may be used as a reducing agent in the reaction of the above reaction scheme 4, the metal boride is $ZrCl_4/NaBH_4$ or $TiCl_4/NaBH_4$, and the borane complex is either a borane forming a complex with dimethylsufide, dibenzylsulfide, diphenylsulfide, THF or 1,4-oxathiane, or $BH_2Cl$ forming a complex with dimethylsulfide. A preferred reducing agent is borane dimethylsulfide complex. The borane complex is used in an amount of 10.0-30.0 molar equivalents, and preferably 12.0-16.0 molar equivalents, relative to the moles of the intermediate containing the thiol substituent.

The solvent that is used in the reaction of the above reaction scheme 4 may be an ether solvent such as tetrahydrofuran. A preferred solvent is tetrahydrofuran. The solvent is used in a volume (ml) equal to 10.0-70.0 times the weight (g) of the intermediate containing the thiol substituent, and preferably in a volume (ml) equal to 35.0-45.0 times the weight (g) of the intermediate.

The reaction of the above reaction scheme 4 may be carried out at a temperature ranging from −5° C. to 30° C., and preferably from 0° C. to 5° C.

The degree of progress of this reaction can be analyzed and determined by, for example, thin film chromatograph or HPLC.

[Reaction scheme 5]

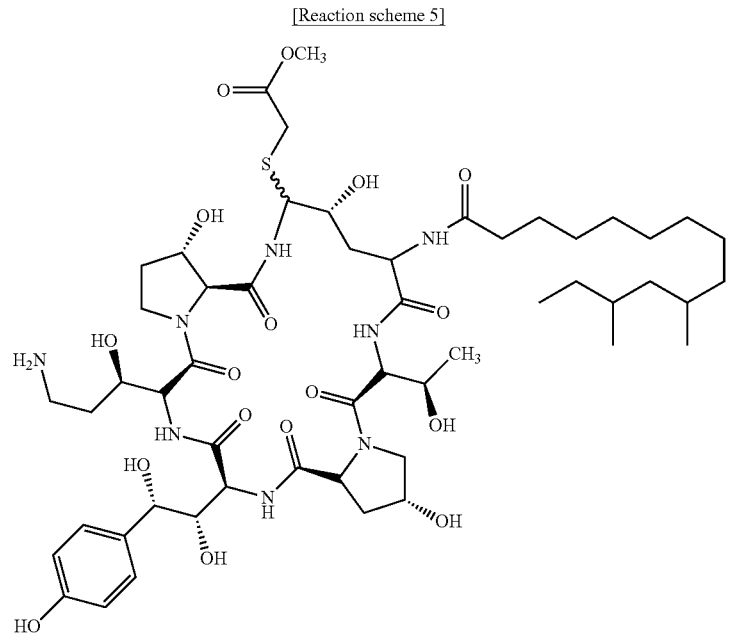

Formula 5
($R_1$ is $CH_2C(\!=\!\!O)OCH_3$)

1) $NH_2CH_2CH_2NH_2$
2) $AcOH/H_2O$
3) RP HPLC
4) EtOAc recrystallization

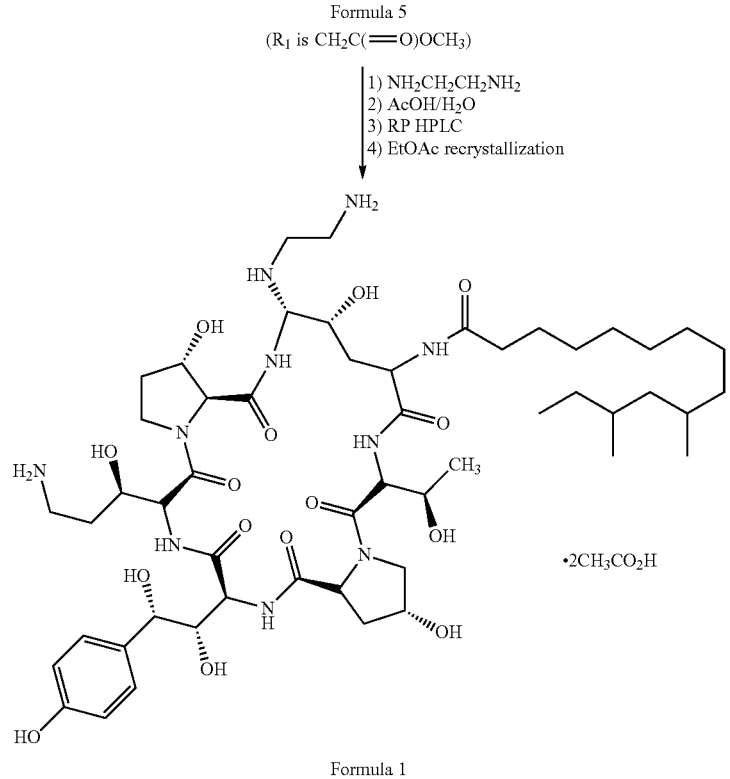

·$2CH_3CO_2H$

Formula 1

As shown in reaction scheme 5 above, 1,2-diaminoethane is added to the intermediate of formula 5, obtained in the previous step, and the mixture is stirred at room temperature for about 2 hours. Then, an aqueous solution of methanol and acetic acid is slowly added dropwise thereto. Purified water is additionally added to the solution, and the resulting solution is washed with n-heptane. Then, the aqueous layer is purified using a medium pressure column packed with RP-C18 adsorbent, thus obtaining a product.

In the reaction of the above reaction scheme 5, substitution with the thio group may be carried out using neat 1,2-diaminoethane or 1,2-diaminoethane dissolved in a suitable solvent. Preferably, neat 1,2-diaminoethane is used. When 1,2-diaminoethane dissolved in the solvent is used, the solvent may be selected from among water; alcohol solvents, such as isopropanol, trifluoroethanol, methanol and ethanol; haloalkane solvents, such as dichloromethane and chloroform; ether solvents such as tetrahydrofuran; and nitrile solvents, such as acetonitrile and propionitrile. A preferred solvent is methanol. The solvent is used in a volume (ml) equal to 1.0-100.0 times the weight (g) of the intermediate containing the thio group, and preferably in a volume (g) equal to 10.0-20.0 times the weight (g) of the intermediate.

The reaction of the above reaction scheme 5 may be carried out at a temperature ranging from 10° C. to 40° C., and preferably from 20° C. to 25° C.

The degree of progress of this reaction can be analyzed and measured by, for example, thin film chromatography or HPLC.

Advantageous Effects

As described above, according to the present invention, through the preparation process of reaction scheme 1 in which a thiol derivative substituted with alkyl and tetrazole is introduced, the pharmaceutically active aza cyclohexapeptide compound, 1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$ (caspofungin), useful as antifungal agents can be prepared at high yield by improving the problem due to a pungent odor and strong toxicity and increasing the production of novel intermediates.

BEST MODE FOR CARRYING OUT THE INVENTION

Hereinafter, the inventive process for preparing the aza cyclohexapeptide compound 1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$ (caspofungin) which is used as an antifungal agent will be described in detail with reference to examples. It is to be understood, however, that these examples are for illustrative purposes only and the scope of the present invention is not limited thereto.

Example 1

Preparation of Compound of Formula 4 Wherein $R_1$ is —$CH_2C(=O)OCH_3$

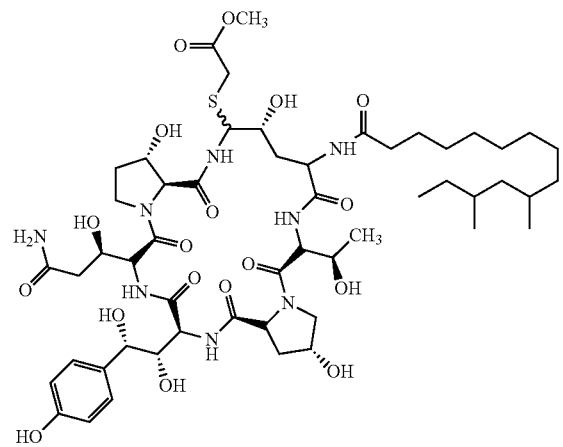

20.0 g of pneumocandin $B_0$ was suspended in 400 ml of acetonitrile, and the solution was cooled to −5° C. 41.9 ml of trifluoroacetic acid was added thereto, and then stirred for 30 minutes, so that the pneumocandin $B_0$ was completely dissolved. Then, 5.98 g of methyl-2-mercaptoacetate was added slowly thereto at a temperature between −5° C. to 0° C., and the mixture was stirred at 0° C. for 6 hours. After completion of the reaction, 1,300 ml of cold purified water was added to the reaction solution to precipitate the crystal. Then, the solution was stirred at a temperature of 0° C. for 1 hour and filtered under reduced pressure, thus separating the crystal from the solution. The obtained crystal was dried in a vacuum, thus obtaining 20.4 g of a light-yellow crystalline compound (yield: 94.2%).

Example 2

Preparation of Compound of Formula 4 Wherein $R_1$ is —$CH_2C(=O)NH(CH_2)_2NH_2$

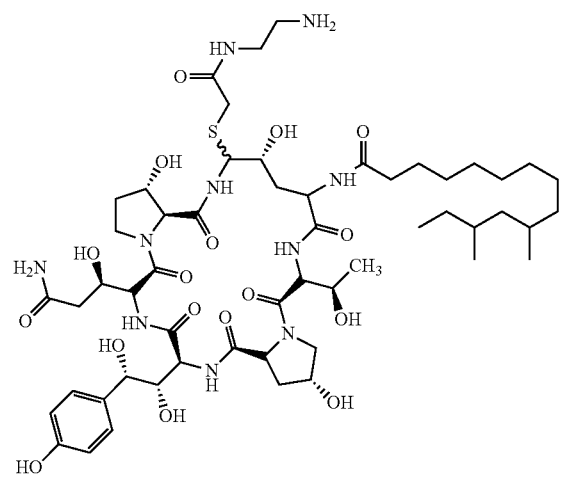

20.0 g of pneumocandin $B_0$ was suspended in 400 ml of acetonitrile, and the solution was cooled to −5° C. 41.9 ml of trifluoroacetic acid was added thereto, and then stirred for 30 minutes, so that the pneumocandin $B_0$ was completely dissolved. Then, 7.57 g of N-(2-aminoethyl-2-mercaptoacetamide was added slowly thereto at a temperature between −5° C. to 0° C., and the mixture was stirred at 0° C. for 10 hours. After completion of the reaction, 1,300 ml of cold purified water was added to the reaction solution to precipitate the crystal. Then, the solution was stirred at a temperature of 0° C. for 1 hour and filtered under reduced pressure, thus separating the crystal from the solution. The obtained crystal was dried in a vacuum, thus obtaining 20.9 g of a white crystalline compound (yield: 94.2%).

Example 3

Preparation of Compound of Formula 4 Wherein $R_1$ is a Tetrazole Ring or a Tetrazole Derivative

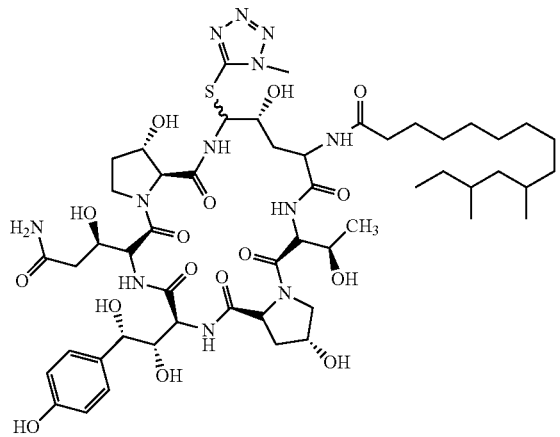

20.0 g of pneumocandin $B_0$ was suspended in 400 ml of acetonitrile, and the solution was cooled to −5° C. 41.9 ml of trifluoroacetic acid was added thereto, and then stirred for 30 minutes, so that the pneumocandin $B_0$ was completely dissolved. Then, 6.55 g of 1-methyl-1H-tetrazole-5-thiol was added slowly thereto at a temperature between −5° C. to 0° C., and the mixture was stirred at 0° C. for 8 hours. After completion of the reaction, 1,300 ml of cold purified water was added to the reaction solution to precipitate the crystal. Then, the solution was stirred at a temperature of 0° C. for 1 hour and filtered under reduced pressure, thus separating the crystal from the solution. The separated crystal was dried in a vacuum, thus obtaining 20.6 g of a white yellow crystalline compound (yield: 94.1%).

Comparative Example 1

Preparation of Phenylthio Pneumocandin $B_0$ Compound 20.0 g of pneumocandin $B_0$ was suspended in 600 ml of acetonitrile, and 4.58 g of phenylboronic acid and 5.80 ml of thiophenol were added thereto. The reaction solution was cooled to −15° C., and 4.98 ml of trifluoromethanesulfonic acid was added thereto. Then, the solution was stirred for 2.5 hours. After completion of the reaction, a solution of 7.66 g of NaOAc.3H$_2$O in 66.6 ml of purified water was added slowly to the reaction solution to precipitate the crystal. Then, the solution was stirred for 2 hours at a temperature of 17° C., and cooled to 0° C. Then, the solution was filtered under reduced pressure, thus obtaining 18.68 g of a phenylthio pneumocandin $B_0$ compound (yield: 88%).

Comparative Example 2

Preparation of 4-methoxyphenylthio pneumocandin $B_0$ compound 25.2 g of pneumocandin $B_0$ was suspended in 630 ml of acetonitrile, and the suspension was cooled to −15° C., after which 5.88 g of 4-methoxythiophenol was added thereto. Then, 117.9 g of trifluoroacetic acid was slowly added dropwise to the solution at a temperature ranging from −15° C. to −10° C., and the resulting solution was stirred at −15° C. for 22 hours. After completion of the reaction, 1,260 ml of purified water was added slowly to the reaction solution at 0° C. or below to precipitate the crystal. Then, the solution was stirred for 1 hour at 0° C. and filtered under reduced pressure, thus separating the crystal from the solution. The separated crystal was dried in a vacuum at 40° C., thus obtaining 23.97 g of the title compound (yield: 85.2%).

TABLE 1

Comparison of processes for preparing the thio pneumocandin $B_0$ intermediate and the results thereof

| | Reaction conditions | Yield |
|---|---|---|
| Example 1 | methyl-2-mercaptoacetate, trifluoroacetic acid | 94.2% |
| Example 2 | N-(2-aminoethyl)-2-mercaptoacetamide, trifluoroacetic acid | 94.2% |
| Example 3 | 1-methyl-1H-tetrazole-5-thiol, trifluoroacetic acid | 94.1% |
| Comparative Example 1 | Thiophenol, phenolboronic acid, trifluoromethanesulfonic acid (U.S. Pat. No. 5,552,521) | 88.0% |
| Comparative Example 2 | 4-methoxythiophenol, trifluoroacetic acid (US 2009/0291996) | 85.2% |

Example 4

Preparation of Compound of Formula 5 Wherein $R_1$ is —CH$_2$C(=O)OCH$_3$

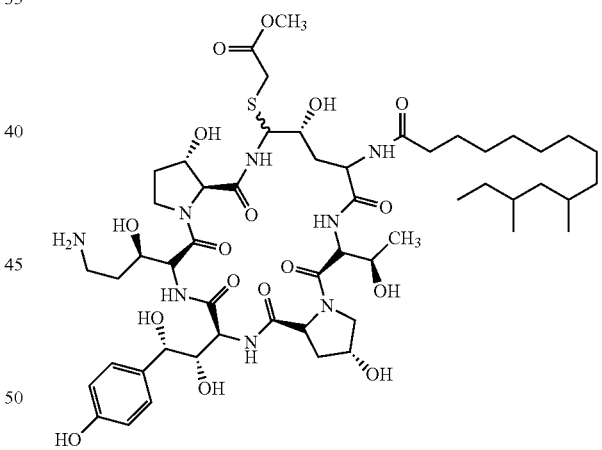

20.0 g of the compound of formula 3 was suspended in 400 ml of acetonitrile, and the solution was cooled to −5° C. 42.4 ml of trifluoroacetic acid was added thereto, and then stirred for 30 minutes, so that the compound of formula 3 was completely dissolved. Then, 6.06 g of methyl-2-mercaptoacetate was added slowly thereto at a temperature between −5° C. to 0° C., and the mixture was stirred at 0° C. for 8 hours. After completion of the reaction, 20 ml of cold purified water was added to the reaction solution to precipitate the crystal. Then, the solution was stirred at a temperature of 0° C. for 1 hour and filtered under reduced pressure, thus separating the crystal from the solution. The separated crystal was dried in a vacuum, thus obtaining 19.8 g of a white crystalline compound (yield: 91.3%).

Example 5

Preparation of Compound of Formula 5 Wherein $R_1$ is —$CH_2C(=O)NH(CH_2)_2NH_2$

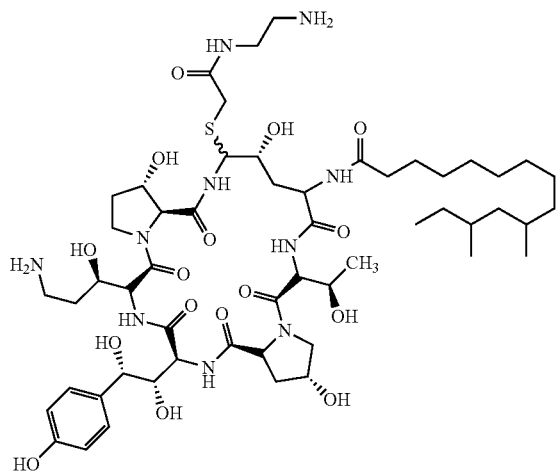

20.0 g of the compound of formula 3 was suspended in 400 ml of acetonitrile, and the solution was cooled to −5° C. 42.4 ml of trifluoroacetic acid was added thereto, and then stirred for 30 minutes, so that the compound of formula 3 was completely dissolved. Then, 7.67 g of N-(2-aminoethyl)-2-mercaptoacetamide was added slowly thereto at a temperature between −5° C. to 0° C., and the mixture was stirred at 0° C. for 8 hours. After completion of the reaction, 20 ml of cold purified water was added to the reaction solution to precipitate the crystal. Then, the solution was stirred at a temperature of 0° C. for 1 hour and filtered under reduced pressure, thus separating the crystal from the solution. The separated crystal was dried in a vacuum, thus obtaining 20.4 g of a white crystalline compound (yield: 91.8%).

Example 6

Preparation of Compound of Formula 5 Wherein $R_1$ is a Tetrazole Ring or a Tetrazole Derivative

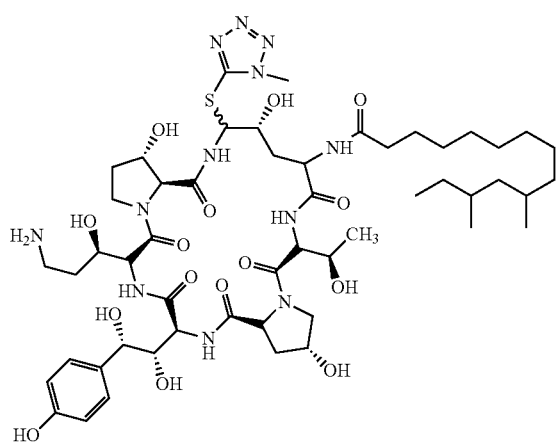

20.0 g of the compound of formula 3 was suspended in 400 ml of acetonitrile, and the solution was cooled to −5° C. 42.4 ml of trifluoroacetic acid was added thereto, and then stirred for 30 minutes, so that the compound of formula 3 was completely dissolved. Then, 6.64 g of 1-methyl-1H-tetrazole-5-thiol was added slowly thereto at a temperature of between −5° C. to 0° C., and the mixture was stirred at 0° C. for 8 hours. After completion of the reaction, 20 ml of cold purified water was added to the reaction solution to precipitate the crystal. Then, the solution was stirred at a temperature of 0° C. for 1 hour and filtered under reduced pressure, thus separating the crystal from the solution. The separated crystal was dried in a vacuum, thus obtaining 20.2 g of a white crystalline compound (yield: 92.4%).

Comparative Example 3

Preparation of Thio Intermediate Compound 5.8 g of the compound of formula 3 was suspended in 230 ml of acetonitrile, and the solution was cooled to −5° C., after which 3.1 g of thiophenol was added. 24.5 ml of trifluoroacetic acid was added thereto at a temperature of 0° C. or below, and then stirred at a temperature between −10° C. and 0° C. for 4 hours. After completion of the reaction, 560 ml of purified water was added to the reaction solution for dilution, and the solution was injected into the top of a medium pressure column packed with 300 g of RP-C18 absorbent. After the injection, the column was washed with 570 ml of purified water and eluted with 500 ml of methanol, and the eluted material was distilled under reduced pressure, thus obtaining 4.1 g of a thio intermediate compound (yield: 61.0%).

TABLE 2

Comparison of processes for preparing the thio intermediate and the results thereof

| | Reaction conditions | Yield |
|---|---|---|
| Example 4 | methyl-2-mercaptoacetate, trifluoroacetic acid | 91.3% |
| Example 5 | N-(2-aminoethyl)-2-mercaptoacetamide, trifluoroacetic acid | 91.8% |
| Example 6 | 1-methyl-1H-tetrazole-5-thiol, trifluoroacetic acid | 92.4% |
| Comparative Example 3 | thiophenol, trifluoroacetic acid (U.S. Pat. No. 5,552,521) | 61.0% |

Example 7

Preparation of Compound of Formula 5 Wherein $R_1$ is —$CH_2C(=O)OCH_3$

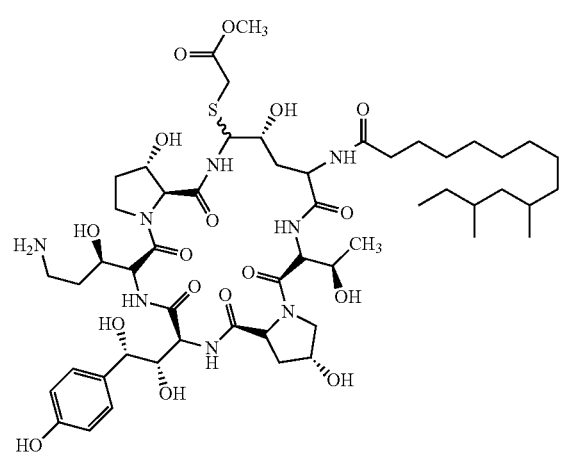

20.0 g of the compound, obtained in Example 1, was suspended in 800 ml of tetrahydrofuran, and 2.12 g of phenylboronic acid was added thereto and completely dissolved, followed by addition of 40.0 g of a molecular sieve. Then, the mixture was stirred at 40° C. for 2 hours and allowed to stand at room temperature for 15 hours. The resulting material was filtered to remove the molecular sieve, and was cooled to 0° C. Then, 21.10 g of a borane dimethylsulfide complex was added slowly thereto over 10 minutes, and the solution was stirred at a temperature between 0° C. and 5° C. for 6 hours. After completion of the reaction, the reaction solution was cooled to −15° C. and neutralized with 66 ml of 2N hydrochloric acid solution. The neutralized solution was diluted with 3000 ml of purified water and injected into the top of a medium pressure column packed with 300 g of RP-C18 adsorbent. After the injection, the column was eluted with 1000 ml of acetonitrile/water (1:4 v/v) and then with 1000 ml of acetonitrile/water (3:2 v/v). Active fractions having a purity of not less than 80% (HPLC peak area %) were combined, and the combined fraction solution was diluted with water to a solution of acetonitrile/water (1:4 v/v) and injected into the top of a medium pressure column packed with 300 g of RP-C18 adsorbent. The desired compound was eluted with 500 ml of methanol, and active fractions having a purity of not less than 85% (HPLC peak area %) were combined and distilled under reduced pressure at 30° C. The residue was added to 120 ml of acetonitrile, stirred for 1 hour, and then allowed to stand at −15° C. for 10 hours, and the produced crystal was separated by filtration under reduced pressure. The separated crystal was vacuum-dried at 30° C., thus obtaining 8.6 g of a white crystalline compound (yield: 43.5%).

Example 8

Preparation of Compound of Formula 5 Wherein $R_1$ is —$CH_2C(=O)NH(CH_2)_2NH_2$

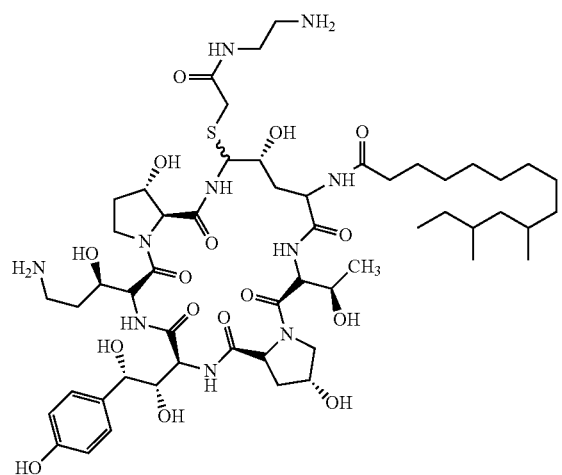

20.0 g of the compound, obtained in Example 2, was suspended in 800 ml of tetrahydrofuran, and 2.07 g of phenylboronic acid was added thereto and completely dissolved, followed by addition of 40.0 g of a molecular sieve. Then, the mixture was stirred at 40° C. for 2 hours and allowed to stand at room temperature for 15 hours. The resulting material was filtered to remove the molecular sieve, and was cooled to 0° C. Then, 20.60 g of a borane dimethylsulfide complex was added slowly thereto over 10 minutes, and the solution was stirred at a temperature between 0° C. and 5° C. for 6 hours. After completion of the reaction, the reaction solution was cooled to −15° C. and neutralized with 64.4 ml of 2N hydrochloric acid solution. The neutralized solution was diluted with 3000 ml of purified water and injected into the top of a medium pressure column packed with 300 g of RP-C18 adsorbent. After the injection, the column was eluted with 1000 ml of acetonitrile/water (1:4 v/v) and then with 1000 ml of acetonitrile/water (3:2 v/v). Active fractions having a purity of not less than 80% (HPLC peak area %) were combined, and the combined fraction solution was diluted with water to a solution of acetonitrile/water (1:4 v/v) and injected into the top of a medium pressure column packed with 300 g of RP-C18 adsorbent. The desired compound was eluted with 500 ml of methanol, and active fractions having a purity of not less than 85% (HPLC peak area %) were combined and distilled under reduced pressure at 30° C. The residue was added to 120 ml of acetonitrile, stirred for 1 hour, and then allowed to stand at −15° C. for 10 hours, and the produced crystal was separated by filtration under reduced pressure. The separated crystal was vacuum-dried at 30° C., thus obtaining 8.5 g of a white crystalline compound (yield: 43.1%).

Example 9

Preparation of Compound of Formula 5 Wherein $R_1$ is a Tetrazole Ring or a Tetrazole Derivative

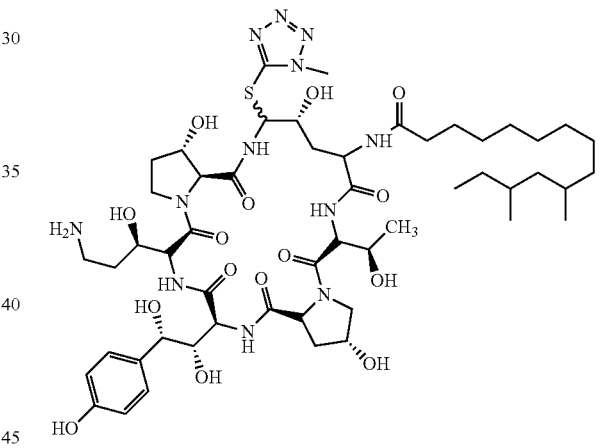

20.0 g of the compound, obtained in Example 3, was suspended in 800 ml of tetrahydrofuran, and 2.10 g of phenylboronic acid was added thereto and completely dissolved, followed by addition of 40.0 g of a molecular sieve. Then, the mixture was stirred at 40° C. for 2 hours and allowed to stand at room temperature for 15 hours. The resulting material was filtered to remove the molecular sieve, and was cooled to 0° C. Then, 20.92 g of a borane dimethylsulfide complex was added slowly thereto over 10 minutes, and the solution was stirred at a temperature between 0° C. and 5° C. for 6 hours. After completion of the reaction, the reaction solution was cooled to −15° C. and neutralized with 65.4 ml of 2N hydrochloric acid solution. The neutralized solution was diluted with 3000 ml of purified water and injected into the top of a medium pressure column packed with 300 g of RP-C18 adsorbent. After the injection, the column was eluted with 1000 ml of acetonitrile/water (1:4 v/v) and then with 1000 ml of acetonitrile/water (3:2 v/v). Active fractions having a purity of not less than 80% (HPLC peak area %) were combined, and the combined fraction solution was diluted with water to a solution of acetonitrile/water (1:4 v/v) and injected into the top of a medium pressure column packed with 300 g of RP-C18 adsorbent. The desired compound was eluted with 500 ml of methanol, and active fractions having a purity of not less than 85% (HPLC peak area %) were combined and distilled under reduced pressure at 30° C. The residue was added to 120 ml of acetonitrile, stirred for 1 hour, and then allowed to stand at −15° C. for 10 hours, and the produced crystal was separated by filtration under reduced pressure. The separated crystal was vacuum-dried at 30° C., thus obtaining 8.7 g of a white crystalline compound (yield: 44.1%).

Example 10

Preparation of Compound of Formula 1

5.0 g of the compound, obtained in Example 7, was suspended in 21.12 ml of 1,2-diaminoethane, and the solution was stirred at room temperature for 2 hours. After completion of the reaction, the reaction solution was added to 50 ml of methanol, and a solution of 46.5 ml of acetic acid in 115 ml of purified water was added dropwise thereto at 20° C. or below. Then, 375 ml of purified water was added thereto, and the solution was washed three times with 100 ml of n-heptane, and the aqueous layer was injected into the top of a medium pressure column packed with 300 g of RP-C18 adsorbent. After the injection, the column was eluted with 3000 ml of acetonitrile/0.15% acetic acid aqueous solution (1:4 v/v), and then active fractions having a purity of not less than 90% (HPLC peak area %) were combined with each other and freeze-dried. Accordingly, 4.3 g (81.2% yield) of the compound of formula 1 as a freeze-dried acetate addition product was obtained.

Example 11

Recrystallization of Compound of Formula 1

2.0 g of the compound, obtained in Example 10, was suspended in 21.73 ml of anhydrous ethanol, and 2.35 ml of purified water was added to dissolve the compound. The solution was filtered under reduced pressure to remove the suspended material, and 0.12 ml of acetic acid was added to the filtrate. Then, 40.0 ml of ethyl acetate was slowly added dropwise thereto to precipitate the crystal. Then, the solution was allowed to stand at room temperature for 4 hours and filtered under reduced pressure to separate the crystal. The separated crystal was washed with 27 ml of ethanol/ethyl acetate/purified water (6/9/0.5 v/v/v) and dried under a nitrogen stream, thus obtaining 1.7 g of a diacetate salt of formula 1 (yield: 85.0%).

$^1$H NMR (CD$_3$OD, 400 MHz): 7.15 (d, J=6.8 Hz, 2H), 6.77 (d, J=6.8 Hz, 2H), 4.63 (m, 6H), 4.27 (m, 5H), 4.07-3.81 (m, 6H), 3.08-2.91 (m, 6H), 2.45 (m, 1H), 2.25 (m, 3H), 2.11-2.01 (m, 5H), 1.92 (s, 6H), 1.62-0.87 (m, 35H)

$^{13}$C NMR (CD$_3$OD, 100 MHz): 10.2, 18.5, 18.8, 19.3, 22.8, 25.7, 26.6, 28.9, 29.2, 29.4, 29.7, 29.8, 31.5, 33.2, 34.3, 35.5, 36.7, 37.1, 37.6, 39.2, 43.3, 44.5, 45.6, 49.8, 54.7, 54.8, 55.7, 57.0, 61.3, 63.0, 66.8, 67.9, 68.7, 69.9, 70.7, 73.7, 74.2, 75.9, 100.0, 114.8, 128.2, 131.6, 157.1, 167.5, 171.3, 171.4, 172.1, 172.2, 172.8, 174.9, 178.9

Yield of Preparation of Caspofungin from Pneumocandin B$_0$

According to the inventive process of preparing caspofungin by introducing a thiol derivative, substituted with alkyl and tetrazole, into pneumocandin B$_0$, caspofungin was obtained at a yield of 28.3%. As can be seen in Table 3 below, this yield was higher than the yields obtained by the prior art processes.

TABLE 3

Comparison of processes for preparing caspofungin from pneumocandin B$_0$ and the yields thereof

| Preparation process | | Overall yield |
|---|---|---|
| U.S. Pat. No. 5,552,521 | pneumocandin B$_0$ → reduction to amine → phenylthio intermediate → substitution with ethylenediamine | 9.6% |
| US 2009/0291996 | pneumocandin B$_0$ → 4-methoxyphenylthio intermediate → reduction to amine → substitution with ethylenediamine | 21.2% |
| US 2008/0319162 | pneumocandin B$_0$ → conversion to cyano group → phenylthio intermediate → substitution with ethylenediamine → reduction to amine | 9.6% |
| The present invention | pneumocandin B$_0$ → thio intermediate → reduction to amine → substitution with ethylenediamine | 28.3% |

The invention claimed is:

1. A process of preparing a compound of the following formula 1 or an acid addition salt thereof comprising the step of reacting a compound of the following formula 5 with 1,2-diaminoethane:

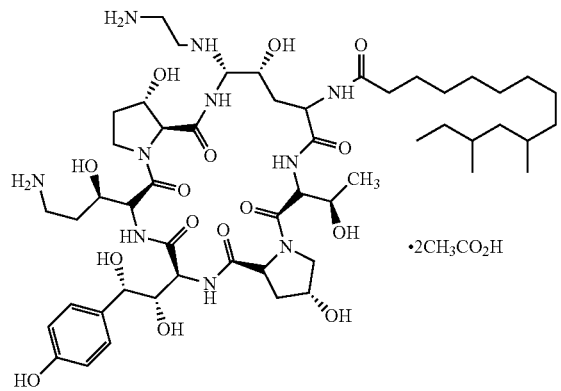

[Formula 1]

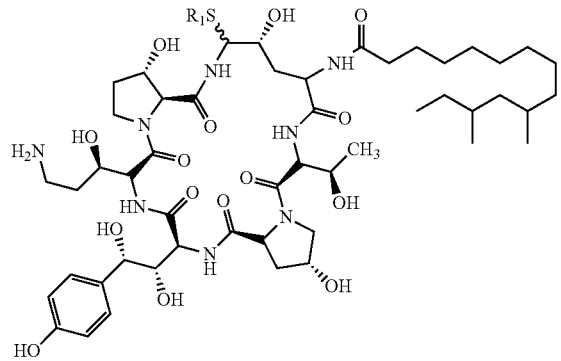

[Formula 5]

wherein R$_1$ is —(CH$_2$)$_n$C(=O)OR$_2$, or —(CH$_2$)$_n$C(=O)NH(CH$_2$)$_m$NH$_2$, wherein R$_2$ is H or C$_1$-C$_3$ alkyl, n=1, 2 or 3, and m=1, 2 or 3.

2. The process according to claim 1, wherein the process further comprises the steps of:
a) reacting a compound of the following formula 2 with a compound of HSR$_1$ to obtain a sulfide compound of the following formula 4; and b) reducing the compound of formula 4 as obtained in step a) to obtain the compound of formula 5:

[Formula 2]

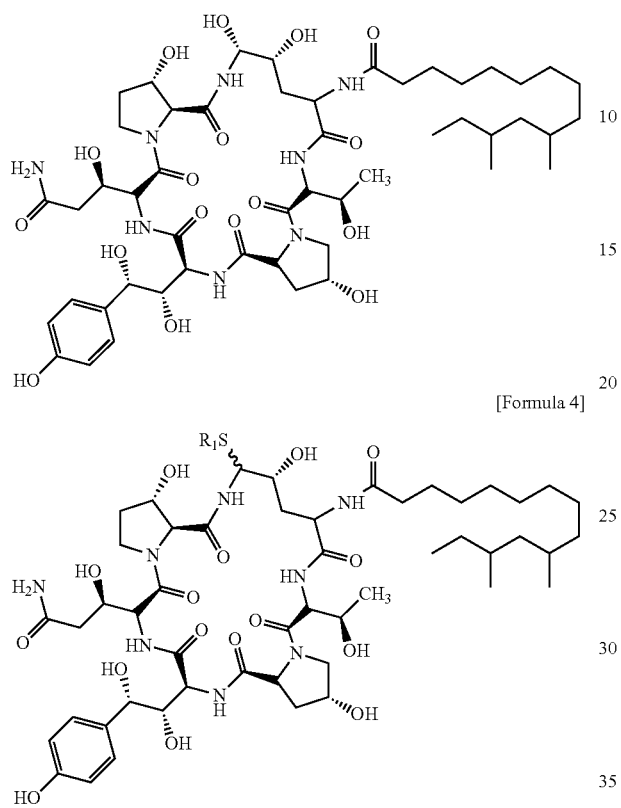

[Formula 4]

wherein $R_1$ is $-(CH_2)_nC(=O)OR_2$, or $-(CH_2)_nC(=O)NH(CH_2)_mNH_2$, wherein $R_2$ is H or $C_1$-$C_3$ alkyl, n=1, 2 or 3, and m=1, 2 or 3.

3. The process according to claim 1, wherein the process further comprises a step of reacting a compound of the following formula 3 with a compound of $HSR_1$, wherein $R_1$ is $-(CH_2)_nC(=O)OR_2$, or $-(CH_2)_nC(=O)NH(CH_2)_mNH_2$, wherein $R_2$ is H or $C_1$-$C_3$ alkyl, n=1, 2 or 3, and m=1, 2 or 3, to obtain the compound of formula 5:

[Formula 3]

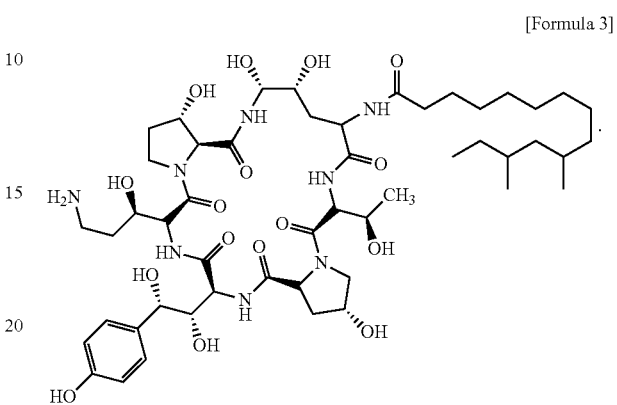

4. The process according to claim 2, wherein the reducing in step b) is carried out using a borane complex or metal boride.

5. The process according to claim 4, wherein the metal boride is $ZrCl_4/NaBH_4$ or $TiCl_4/NaBH_4$, and the borane complex is either a borane forming a complex with dimethylsulfide, dibenzylsulfide, diphenylsulfide, THF or 1,4-oxathiane, or $BH_2Cl$ forming a complex with dimethyl sulfide.

6. The process according to claim 1, wherein the reaction with 1,2-diaminoethane is carried out using neat 1,2-diaminoethane or 1,2-diaminoethane dissolved in a solvent.

7. The process according to claim 6, wherein the solvent is selected from among water, methanol, ethanol, tetrahydrofuran, isopropanol, trifluoroethanol, acetonitrile and dichloromethane.

* * * * *